April 18, 1950 G. OHLHUS Plant Pat. 935
ROSE PLANT
Filed Nov. 19, 1948
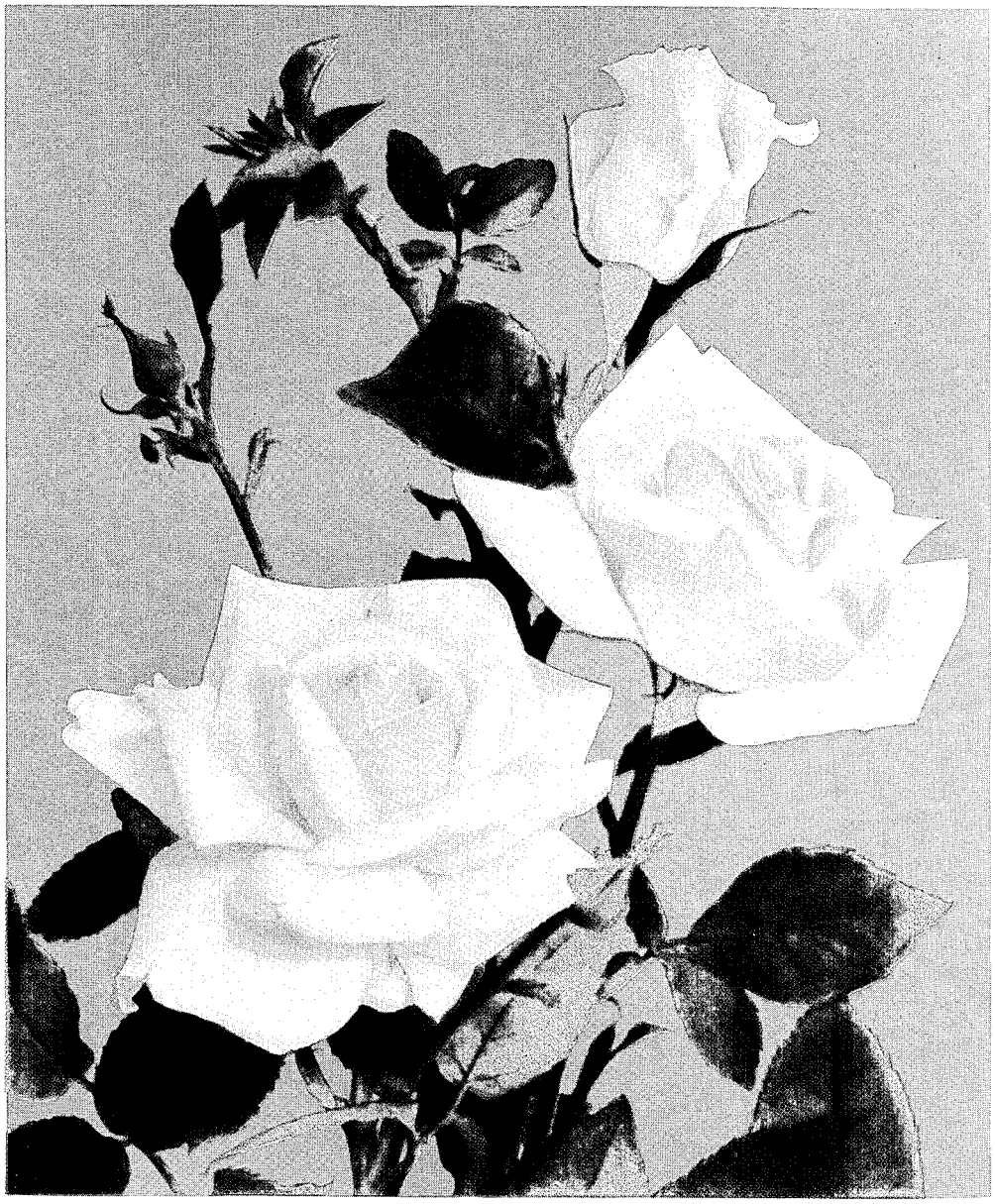
Inventor
George Ohlhus
By Robbs & Robbs
Attorneys Patented Apr. 18, 1950

Plant Pat. 935

UNITED STATES PATENT OFFICE

935

ROSE PLANT

George Ohlhus, West Grove, Pa., assignor to The Conard-Pyle Company, West Grove, Pa., a corporation of Pennsylvania Application November 19, 1948, Serial No. 60,899

1 Claim. (Cl. 47—61)

The present invention relates to a new and distinct variety of rose plant, resulting from careful breeding with the object of producing a rose suitable for both outdoor or garden decoration and cut-flower purposes.

By using the particular parents, I obtained a very strong, erect growing plant that produces large and very double open blooms, remarkably long lasting and of a rich tinting of tones of pink color and at times pleasing, strong fragrance. The great beautifully furled buds open slowly with the individual petals large and of heavier texture than commonly found in so double a rose. The full blooms are excellent, each petal tip curling back to form a perfect point, perfectly arranged around the high, furled center. The large blooms are held erect on very firm, strong stems on tall, vigorous plants. The long lasting characteristic prevails on the bush as well as in their use as cut-flowers.

This combination of characteristics is very desirable in roses of the particular tone because of their attractive contrasting high lights in any setting, whether outdoors or inside.

Asexual reproduction of this new variety shows the foregoing characteristics come true to form and are established.

The accompanying drawing illustrates the distinctive characteristics of the flowers at different stages of development from bud to full blown blossoms.

The following is a detailed description of the new variety, all reference to color being in accordance with Ridgway's Color Standards and Nomenclature and ordinary dictionary definition:

Type: Hardy; bush; outdoor; seedling; for cut-flowers and garden decoration.
Class: Hybrid tea.
Breeding: Seedling.
*Seed parent.*—"Soeur Therese."
*Pollen parent.*—Unnamed ("Duquesa de Penaranda" × "Mrs. Pierre S. du Pont").
Propagation: Holds its distinguishing characteristics through succeeding propagations by budding.

*Flower*

Locality where grown: West Grove, Pennsylvania.
Flowers borne: Singly to stem; on strong, medium long stems.
Quantity of bloom: Free; abundant outdoors.
Continuity: Continuous.
Fragrance: Intermittent; tea.

Bud:
*Peduncle.*—Medium length; medium heavy; erect; almost smooth; few green hairs. Color—Lettuce Green, Plate V.
*Before calyx breaks.*—Size—medium. Form—pointed; with foliaceous appendages on the surface of the bud; with slender cut foliaceous parts extending beyond the tip of the bud equal to one-half or less of its length.
*As calyx breaks.*—Color—Old Rose, Plate XIII.
*As first petal opens.*—Size—medium. Form—ovoid. Color—outside: shading from Light Dull Green-Yellow, Plate XVII, at tip of base, to Thulite Pink, Plate XXVI, and to Light Spinel Red, Plate XXVI, at outer edges; inside: shading from Light Green-Yellow, Plate V, at base to Thulite Pink, Plate XXVI, and to Spinel Red, Plate XXVI, at outer edges.
*Opening.*—Opens up well.
Bloom: Size, when fully open—4¾ inches to 5¼ inches.
*Petalage.*—Very double; from 40 to 70 petals; arranged regularly.
*Form.*—Very high center at first; becoming high centered; petals remaining at first very loosely rolled outward; becoming later, at maturity, loosely rolled outward.
Petals: Leathery; with inside and outside satiny.
*Shape.*—Outside—obovate. Intermediate—obovate. Inside—obovate.

This description of a newly opened flower was made from a rose grown outdoors in the month of August, at West Grove, Pennsylvania:

*Color.—Outside petal*—outside surface: Rose Color, Plate XII; inside surface: Deep Rose Pink, Plate XII. *Intermediate petal*—outside surface: Deep Rose Pink, Plate XII; inside surface: Deep Rose Pink, Plate XII. *Inner petal*—outside surface: Deep Rose Pink, Plate XII; inside surface: Deep Rose Pink, Plate XII.

This description was made from a rose that was open for three days outdoors in the month of August, at West Grove, Pennsylvania:

*Color. — Outside petal* — outside surface: shading from white at base to Deep Rose Pink, Plate XII, over most of the petal surface; inside surface: shading from white at base to Deep Rose Pink, Plate XII, over most of the petal surface. *Inside petal*—outside surface: Deep Rose Pink, Plate XII; inside surface: Deep Rose Pink, Plate XII.

*General color effect.*—Newly opened flower—Deep Rose Pink, Plate XII. Three days open—Deep Rose Pink, Plate XII.

*Behavior.*—Drop off cleanly.

*Flower longevity.*—Cut roses grown outdoors kept at living-room temperatures four to five days in August.

*Reproductive organs*

Stamens: Medium number; most arranged regularly about pistils, occasionally a few mixed with petaloids.

Filaments: Medium length; most with anthers. Color—Light Coral Red, Plate XIII.

Anthers: Medium size; all open at various times; occasionally an anther fused with a petaloid or with a pistil.

Pollen: Moderately abundant. Color—Orange, Plate III.

Pistils: Many.

Styles: Uneven; medium length; medium heavy; bunched.

Stigma: Color—Sulphur Yellow, Plate V.

Ovaries: Some protruding from calyx.

Hips: Ovoid; moderately smooth; medium thick. Color—Courge Green, Plate XVII.

Sepals: Permanent; moderately long; spear-shaped.

Seeds: Medium number; medium size.

*Plant*

Foliage:

*Leaves.*—Compound of three or five leaflets; abundant; medium size; leathery.

*Leaflets.*—Shape—oval with apex acute; base round; margin simply serrate.

*Color.*—*Mature*—upper surface: Dark Cress Green, Plate XXXI; under surface: Asphodel Green, Plate XLI. *Young*—upper surface: Parrot Green, Plate VI, bordered with Prussian Red, Plate XXVII; under surface: Yellowish Oil Green, Plate V, veiled with Indian Red, Plate XXVII.

*Rachis.*—Medium heavy. Upper side: grooved; under side: moderately thorny.

*Stipules.*—Moderately long; moderately narrow; with medium long points turning out at an angle of less than 90°.

*Disease.*—Resistant to mildew and blackspot.

Growth:

*Habit.*—Upright; branched.

*Growth.*—Vigorous.

*Canes.*—Heavy.

*Main stems.*—Dull green sometimes shaded with red. *Thorns*—several; medium length; hooked downward; with long narrow base. *Prickles and hairs*—none.

*Branches.*—Dull green sometimes shaded with red. *Thorns*—several; medium length; hooked downward; with medium length narrow base. *Prickles*—several; reddish. *Hairs*—none.

*New shoots.*—*Color*—Oil Green, Plate V. *Thorns*—several; medium long; hooked downward; with narrow base. *Prickles*—several; reddish. *Hairs*—none.

I claim:

A new and distinct variety of rose plant, characterized as to novelty by its strong and erect habits of growth, and its production of blooms of a rich tinting of pink color tones, very double, large size and of long lasting quality, substantially as shown and described.

GEORGE OHLHUS.

No references cited.